(12) United States Patent
Sturm et al.

(10) Patent No.: US 6,350,869 B1
(45) Date of Patent: Feb. 26, 2002

(54) CRYSTALLINE AMINE SALT OF CEFDINIR

(75) Inventors: Hubert Sturm, Innsbruck; Siegfried Wolf, Brixlegg; Johannes Ludescher, Breitenbach, all of (AT)

(73) Assignee: Biochemie Gesellschaft m.b.H., Kundl (AT)

( * ) Notice: Subject to any disclaimer, the term of this patent is extended or adjusted under 35 U.S.C. 154(b) by 0 days.

(21) Appl. No.: 09/381,947

(22) PCT Filed: Apr. 2, 1998

(86) PCT No.: PCT/EP98/01953

§ 371 Date: Sep. 27, 1999

§ 102(e) Date: Sep. 27, 1999

(87) PCT Pub. No.: WO98/45299

PCT Pub. Date: Oct. 15, 1998

(30) Foreign Application Priority Data

Apr. 4, 1997 (AT) ................................................ 570/97

(51) Int. Cl.⁷ ...................... C07D 501/12; C07D 501/22

(52) U.S. Cl. ......................... 540/220; 540/222; 540/220

(58) Field of Search .................................. 540/222, 220

(56) References Cited

U.S. PATENT DOCUMENTS

| 4,559,334 A | 12/1985 | Takaya et al. | ............... 514/202 |
| 5,869,648 A | * 2/1999 | Ludescher | .................. 540/215 |

FOREIGN PATENT DOCUMENTS

| EP | 0 304 019 B1 | 2/1989 |
| GB | 1 038 529 | 8/1966 |
| WO | 97/07121 | 2/1997 |
| WO | 97/24358 | 7/1997 |
| WO | 98/06723 | * 2/1998 |

* cited by examiner

*Primary Examiner*—Mark L Berch
(74) *Attorney, Agent, or Firm*—Lydia T. McNally; Susan Hess

(57) ABSTRACT

Cefdinir in the form of a salt with dicyclohexylamine, a process for its production and its use in the purification of impure cefdinir.

3 Claims, No Drawings

CRYSTALLINE AMINE SALT OF CEFDINIR

The present invention relates to intermediates in the purification of cefdinir, i.e. 7-(Z)-[2-(2-acinothiazol)-4-yl)-2-hydroxyiminoacetamido]-3-vinyl-3-cephem4-carboxylic acid of formula

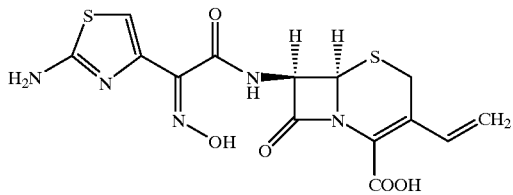

Cefdinir may be used, e.g. in form of a monohydrate, as a pharmaceutical, e.g. antibiotic; see e.g. Y. Inamoto, Toshiyuki Chiba, Toshiaki Kiamimura und Takao Takaya, J. Antibiotics Vol XLI, No 6, 829, (1988).

Cefdinir may be obtained in impure form according to known production processes. It was now surprisingly found that impure cefdinir may be purified via the formation of a salt, e.g. in crystalline form, thereof.

In one aspect the present invention provides a compound of formula I in the form of a salt, e.g. crystalline, with dicyclohexylamine.

A compound of formula I in the form of a salt with dicyclohexylamine may be produced as follows:

Cefdinir, e.g. in the form of a solvate, such as a hydrate, e.g. in impure form, e.g. as obtained in a production process of cefdinir, such as a mixture of cefdinir and impurities, e.g. such as a mixture of by-products originating from the production process of cefdinir and cefdinir; may be treated in the presence of a solvent, e.g. in dissolved or suspended form, with dicyclohexylamine. A solvent includes any solvent which is inert towards cefdinir or towards cefdinir in the form of a salt with dicyclohexylamine, e.g. a polar organic solvent, such as amides, e.g. dimethylformamide; alcohols, e.g. methanol or ethanol; ketones, e.g acetone; e.g. in combination with water and water. A solvent system, e.g. mixtures of individual solvents, e.g. as described above may be used. A preferred solvent system may be e.g. acetone/water, including e.g. a ratio of about 100:1 such as 50:1, e.g. 20:1 to 1:5; such as 10:1 to 1:3, e.g. 5:1 to 2:1, e.g. about 1:1. Per equivalent of cefdinir about one equivalent or more, such as 5; e.g. 3, such as 2 equivalents of dicyclohexylamnine may be used, e.g. combined with the mixture of impure cefdinir in a solvent. A compound of formula I in the form of a salt with dicyclohexylamnine may crystallize e.g. from a reaction solution, or, e.g. a suspension of a compound of formula I in a solvent may be converted into a crystal suspension of a compound of formula I in the form of a salt with dicyclohexylamine. An anti-solvent may be added to the reaction mixture, e.g. in order to complete crystallization. An anti-solvent includes solvents wherein a compound of formula I in the form of a salt with dicyclohexylamine is insoluble or soluble only to a small extent if added to the solution or suspension of a compound of formula I in the form of a dicyclohexylamine, e.g. A polar solvents; e.g. ethers, such as diethylether, tetrahydrofurane; or a ketone, e.g. acetone. A compound of formula I in the form of a salt with dicyclohexylamine may be isolated from the reaction mixture, e.g. as conventional, e.g. by filtration, centrifugation.

A compound of formula I in the form of a salt with dicyclohexylamnine may be obtained in pure f form, e.g. in 98% purity and more, such as 99% to 100% purity; e.g. the amount of impurities present in cefdinir in impure form used for salt formation may be decreased; e.g. impurities of 10% and more in cefdinir in impure form may be decreased to impurities of 1 % and less, e.g. 0 to 1% in cefdinir in the form of a salt with dicyclohexylamine.

A compound of formula I in the form of a salt with dicyclohexylamine may be further purified by re-suspension or re-dissolution as described above, e.g. in an (anti) solvent (system), e.g. as described above.

In another aspect the present invention provides a process for the production of a compound of formula I in the form of a salt with dicyclohexylamrine, e.g. in crystalline form, comprising treating a compound of formula I, e.g. in form of a solvate, such as a hydrate, in a solvent with dicyclohexylamine and isolating a compound of formula I in the form of a salt with dicyclohexylamine, e.g. in crystalline form.

Cefdinir in free form, e.g. in the form of a solvate, such as a hydrate, e.g. monohydrate and in purified form, e.g. in respect with impure cefdinir used for the formation of a salt of a compound of formula I with dicyclohexylarnine, may be obtained from a compound of formula I in the form of a salt with dicyclohexylamine, e.g. as conventional for setting free a compound which is in the form of a salt, e.g. in the form of an amine salt; e.g. by adjusting an appropriate pH, e.g. 1.5 to 4, such as 2 to 3; of a mixture, e.g. a solution, of cefdinir in the form of a salt with dicyclohexylamine with a solvent, e.g. in the presence of water, preferably in water, e.g. by addition of an acidic agent, such as an organic or inorganic acid, preferably an inorganic acid, e.g. sulphuric acid. Cefdinir, e.g. in the form of hydrate, e.g. monohydrate may crystallize and may be isolated, e.g. as conventional, e.g. by filtration, centrifugation. A compound of formula I may be obtained according to the process of the present invention as such or in the form of a solvate, e.g. a hydrate, e.g. a monohydrate. A compound of formula I obtained according to the process of the present invention as such may be converted into a compound of formula I in the form of a solvate, e.g. a hydrate, such as a monohydrate and vice versa.

In another aspect the present invention provides a process for the production of a compound of formula I, e.g. in form of a solvate, such as a hydrate, eg. monohydrate comprising converting a compound of formula in the form of a salt with dicyclohexylamine, e.g. in crystalline form, into a compound of formula I, e.g. in the form of a solvate, and isolating a compound of formula I, e.g. in the form of a solvate.

In another aspect the present invention provides a process for the purification of cefdinir in a mixture of a compound of formula I with impurities, comprising forming a salt of a compound of formula I with dicyclohexylamine; and converting a compound of formula I in the form of a salt with dicyclohexylarine, e.g. in crystalline form, into a compound of formula I, e.g. in the form of a solvate, and isolating a compound of formula I, e.g. in the form of a solvate.

A compound of formula I in the form of a salt with dicyclohexylamine is useful in the purification of cefdinir in impure form.

In another aspect the present invention provides the use of a compound of formula I in the form of a salt with dicyclohexylarine, e.g. in crystalline form in the purification of a mixture of a compound of formula I with impurities.

The present invention has several surprising advantages:

A compound of formula I in the form of a salt with dicyclohexylamine may be in a crystalline form; cefdinir in the form of a salt may be obtained in surprising high purity, e.g. 98% purity and more, e.g. 98% to 100%; production of the salt is simple; cefdinir obtained from the salt may be surprisingly pure, e.g. 98% and more, e.g. 99% to 100%.

It is surprising that cefdinir under the basic conditions of the salt formation according to the present invention is stable, because from e.g. Yoshihiko Okamoto et al., J. of Pharmaceutical Sciences, Vol 8S, No 9, 976, (1996) it is known that cefdinir may be instable in a basic environment; it was e.g. found that cefdinir in the presence of other amines, e.g. tert.-octylamine under similar conditions may be, e.g. heavily, degraded.

In another aspect the present invention provides crystalline 7-(Z)-[2-(2-aminothiazol4-y1)-2-hydroxyiminoacetamido]-3-vinyl-3-cephem-4carboxylic acid/dicyclohexylammonium salt of formula

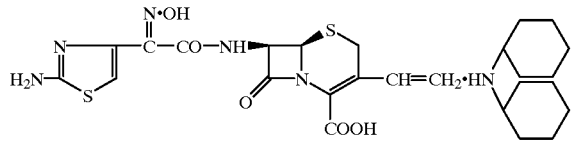

In the following examples, which illustrate the invention more fully but do in no way limit its scope, all temperatures are given in degrees Celsius. Purity of a compound obtained is determined by HPLC.

EXAMPLE 1

7-(Z)-[2-(2-Aminothiazol-4-yl)-2-hydroxyianoacetanido]-3-vinyl-3-cephem-4carboxylic acid in form of a salt with dicyclohexylarnine 10 g of crude cefdinir, e.g. as obtained in a cefdinir production process, in 50 ml of water and 50 ml of acetone are treated under stirring with 5 ml of dicyclohexylamine. A solution is obtained and 7-(Z)-[2-(2-Aminothiazol-4-yl)-2-hydroxyimino acetamido]-3-vinyl-3-cephem-4-carboxylic acid in form of a salt with dicyclohexylarnine crystallizes. 250 ml of acetone are added to the crystal suspension which is stirred for ca. 30 minutes at room temperature. The crystalls are filtrated off, wash ed with a ce tone and dried. Crystalline 7-(Z)-[2-(2-Aminothiazol-4-y1)-2-hydroxyimnoacetamido]-3-vinyl-3-cephem-4-carboxlic acid in form of a salt with dicyclohexyla9ine in a purity of 98.6 % is obtained. Mp: 175° (decomposition). $^1$H-NMR (DMSO-$d_6$): 9.41 (d, 1H, J=8.1 Hz, NH); 7.12 (s, 2H, NH$_2$); 6.99 (dd, 1H, J=11.4 and 17.7 Hz, CH=CH$_2$); 6.64 (s, 1H, thiazol); 5.60 (dd, 1H, J=4.8 and 8.1 Hz, H$_7$); 5.15 (d, 1HJ=17.7 Hz, CH=CH$_2$); 5.04 (d, 1H, J=4.8 Hz, H$_6$); 4.94 (d, 1H, J=11.4 Hz, CH=CH$_2$); 3.52, 3.39 (AB d, 1H, J=17 Hz, H$_2$); 3.21 (m, 2H); 2.05 (m, 4H); 1.8 (m, 4H); 1.6 (m, 2H); 1.2–1.4 (m, 10H).

EXAMPLE 2

7-(Z)-[2-(2-Aminothiazol-4-yl)-2-hydroxyimino-acetamido]-3-vinyl-3 -cephem-4-carboxyic acid in the form of a monohydrate 10 g of 7-(Z)-[2-(2-Aminothiazol-4-yl)-2hydroxyimino-acetamido]-3-vinyl-3-cephem-4-carboxylic acid in form of a salt with dicyclohexylarne, obtained according to Example 1 are dissolved in 175 ml of water at a temperature of ca. 35–40° and treated with active charcoal. Active charcoal is filtrated off and the pH of the solution obtained is adjusted to pH 2.5 by addition of 5 ml of sulphuric acid at ca. 35°. 7-(Z)-[2-(2-Aminothiazol-4-yl)2hydroxyimino acetarrido]-3-vinyl-3-cephem4-carboxylic acid in the form of a monohydrate precipitates, is filtrated off, washed with water and dried. 7-(Z)-[2(2-Aminothiazol-4-yl)-2-hydroxyimino acetamido]-3-vinyl-3cephem-4-carboxylic acid in the form of a monohydrate in a purity of 99% is obtained.

EXAMPLE 3

Production of Crude Cefdinir 40 g of 7-amino-3-vinyl-3-cephem-4-carboxylic acid in 400 ml of dichloromethane are treated with 55.7 ml of N,O-bistnmethyl-silylacetamid. The mixture obtained is stirred for ca. 2 hours at room temperature, cooled to 0° and treated with 52.2 g of 2-(Z)-(2-aminothiazol-4-yl)-2-acetoxyiminoacetic acid chloride in the form of a hydrochloride in small portions. The mixture obtained is stirred for ca.90 minutes at 0° and added under stirring to a mixture of 44.55 g of NaHCO$_3$, 600 ml of water und 100 ml of dichloromethane of a temperature of 5°. The pH of the mixture obtained is adjusted to a pH of ca. 7.2–7.3 with a saturated aqueous solution of NaHCO$_3$. The phases formed are separated. To the aqueous phase 300 ml of water are added and 28.7 g of NH$_4$Cl. The pH of the mixture obtained is adjusted to pH 8 by addition of an aqueous 10% K$_2$CO$_3$ solution and the mixture is stirred for ca. 80 minutes. A solution is obtained. The pH of the solution obtained is adjusted to pH 3 by addition of 5 m sulphuric acid. 7-(Z)-[2-(2-amino-thiazol4-yl)-2-hydroxyiminoacetamido]-3-vinyl-3-cephem-4-carboxylic acid precipitates, is filtrated off, washed with water and dried. 7-(Z)-[2-(2-amino-thiazol-4-yl)-2-hydroxyiminoacetamido]-3-vinyl-3-cephem-4-carboxylic acid in a purity of 94.3 % is obtained.

What is claimed is:

1. A process for the purification of a compound of formula I

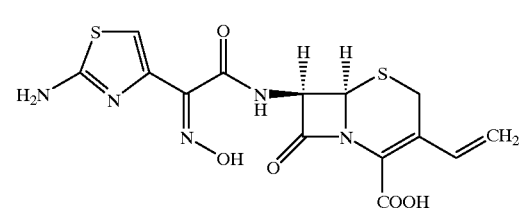

in a mixture of a compound of formula I with impurities, comprising
   i. treating a compound of formula I in a solvent with dicyclohexylamine to form a compound of formula I in the form of a salt with dicyclohexylamine;
   ii. isolating said dicyclohexylamine salt of a compound of formula I
   iii. treating the compound of formula I in the form of a salt with dicyclohexylamine with an acidic agent to form a compound of formula I; and
   iv. isolating the compound of formula I.

2. A process for the production of a compound of formula I,

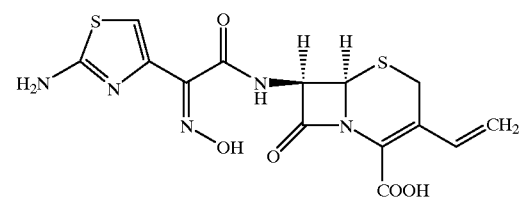

wherein the compound of formula I is in the form of a solvate, comprising
   (i) treating a compound of formula I in the form of a salt with dicyclohexylamine with an acidic agent to form a compound of formula I, and
   (ii) isolating said compound of formula I in the form of a solvate.

3. A process according to claim 1 wherein the compound of formula I is in the form of a solvate.

* * * * *